United States Patent
Horn (10) Patent No.: US 7,919,971 B2
(45) Date of Patent: Apr. 5, 2011

(54) METHOD AND DEVICE FOR MEASURING THE CONDITION OF STEEL STRUCTURES

(76) Inventor: Harald Horn, Trondheim (NO)

(*) Notice: Subject to any disclaimer, the term of this patent is extended or adjusted under 35 U.S.C. 154(b) by 756 days.

(21) Appl. No.: 11/909,517

(22) PCT Filed: Mar. 29, 2006

(86) PCT No.: PCT/NO2006/000116
§ 371 (c)(1),
(2), (4) Date: Sep. 28, 2007

(87) PCT Pub. No.: WO2006/107210
PCT Pub. Date: Oct. 12, 2006

(65) Prior Publication Data
US 2010/0163433 A1  Jul. 1, 2010

(30) Foreign Application Priority Data
Apr. 5, 2005  (NO) .................................... 20051674

(51) Int. Cl.
*G01R 27/08* (2006.01)
(52) U.S. Cl. ........................................................ 324/700
(58) Field of Classification Search ............ 324/700
See application file for complete search history.

(56) References Cited

U.S. PATENT DOCUMENTS

| | | | | |
|---|---|---|---|---|
| 4,523,250 A | * | 6/1985 | Bacchiere et al. | 361/145 |
| 4,656,595 A | * | 4/1987 | Hognestad | 702/38 |
| 5,684,406 A | * | 11/1997 | MacLauchlan et al. | 324/700 |
| 5,895,843 A | * | 4/1999 | Taylor et al. | 73/86 |
| 5,940,362 A | * | 8/1999 | Plonsky et al. | 369/273 |
| 6,223,129 B1 | * | 4/2001 | Chan et al. | 702/30 |
| 2003/0184322 A1 | * | 10/2003 | Hands | 324/700 |
| 2005/0168208 A1 | * | 8/2005 | Pots et al. | 324/72.5 |

* cited by examiner

*Primary Examiner* — Jeff Natalini
(74) *Attorney, Agent, or Firm* — Dennison, Schultz & MacDonald (57) ABSTRACT

Method and apparatus for measuring parameters in ferromagnetic steel structures, e.g. railway rails and drill pipes, to detect mechanical stress, damage and deterioration. On the monitored structure, devices for magnetization or demagnetization e.g. an electromagnet, will be installed. Two or more electrodes for feeding of a pulse shaped electrical voltage are installed. Across another pair of electrodes, a voltage response signal is measured, and compared with another response signal measured under known conditions or compared with calibration data for the structure. The deviation between these voltages is analyzed to quantify the relative or absolute deviations, and the condition of the steel structure is estimated. The device can measure the transient voltage curves with reference to one or more of the magnetization curves and includes algorithms for analyzing the voltage response curve for determination of mechanical stress and/or fatigue and/or cracks and/or metal loss in steel materials.

13 Claims, 5 Drawing Sheets

METHOD AND DEVICE FOR MEASURING THE CONDITION OF STEEL STRUCTURES

BACKGROUND OF THE INVENTION

The present invention is directed to a method for measuring the condition of a steel structure. Furthermore, it comprises a device for carrying out such measurements of condition of a steel structure. The method can be adapted for detection of mechanical stress, fatigue and metal loss e.g caused by corrosion.

More particularly the invention concerns a method for measuring the condition of a steel structure, whereby a pulse-shaped electrical current is applied to the steel through a pair of contact points, generating potential drop curves between another pair of contact points measured by repeated sampling. The steel subjected to the measurements can both be magnetized and demagnetized by means of arrangements known per se and being employed for magnetization of the steel to selected points at the initial, the anhysteretic and hysteretic magnetization curves. Comparison of the potential drop curves at different magnetization makes it possible to determine the condition of the steel or change of condition. Change of some types of conditions may be measured without using magnetization means, in such cases the method also can be applied for monitoring of all types of electrically conductive materials.

Large steel structures are often subjected to varying loads causing deterioration. For safety reasons it is important to inspect and monitor such structures in order to discover conditions which can develop into serious defects, among these conditions being mechanical stresses, corrosion and erosion.

Mechanical stress can arise unintentionally both during construction, (for example in or adjacent to weld seams) and during operation because of uncontrollable conditions.

For measuring relative mechanical stresses strain gauges or other means are often employed for detecting small dimensional changes in the steel. By using of such methods changes are measured from the instant the arrangement is installed with respect to absolute mechanical stresses the possibilities are more limited. It is known, however, that measurement and analysis of Barkhausen noise can provide information about mechanical stresses. (Rautioaho, R. H., and Karjalinen, L. P.: "Application of Barkhausen noise measurements to residual stress analysis in structural steels". Proc. Scandinavian Symposium in Materials Science, 20-21 Jun. 1983, Oulu Finland, pp 179-185.)

Moreover it is to be noted that mechanical stresses lead to changes in magnetic properties and use of this phenomenon has been attempted as a basis for measuring mechanical stresses in steel. (Lugg M. C: The effect of stress on the ACFM technique". Controller C HMSO, London 1987.).

A method based on measuring the stationary voltage or potential drop from the excitation of a pulse shaped current is known from the Norwegian patent no. 150136.

The voltage drop is measured between a number of contact points both when the structure is in a preferably known initial condition and during operation. The voltage drops measured are compared with each other and form the basis for detecting changes in the condition of the structure caused by cracks and material loss.

The current applied is pulse shaped. Upon each current step the voltage drop measured will follow a transient curve because of the skin effect, which in the above patent is referred to as disturbances, and the method assumes that the transient portion of the voltage drop has decayed before measurement takes place. Thus, according to the patent a prejudice exists against the consideration of the transient portion of the voltage drop curve to provide information on possible defects or changes in the structure. The disadvantage is that for large pipes with large wall thickness the transient time is long and for practical applications and for other reasons measurements are made before the transient has decayed. These measurements are thus influenced by changes in the ferromagnetic properties caused by changes in the structures' stress or pipes' internal pressure, which are regarded as disturbances in the measurement of corrosion or cracks.

Norwegian patent specification 172868 describes a method to measure mechanical stress and fatigue in steel. This patent mainly describes a method based on measuring the transient voltage response from a pulse shaped excitation current. Two such transient voltage drops are measured between a number of contact points for different conditions of the structure. The measured transient voltages are compared and make the basis for computation of the mechanical stress and degree of fatigue. However, this patent does not describe how the method responds to fatigue. Furthermore, these measurements do not consider the information inherent in the stationary part of the voltage response, which includes significant information about the fatigue.

SUMMARY OF THE INVENTION

The main object of this invention is to provide a method for monitoring different types of structures, and which enables detection of conditions that can cause defects sooner than with known methods. It is possible with this method to detect at the earliest possible time, changes in the steel caused by excessive loads and e.g. detect micro cracks in the surface, caused by such loads, and thus, at the earliest possible time, to determine the degree of deterioration caused by such loads.

Detection sensitivity and quantification of cracks will be improved compared to known methods, and also reliability and accuracy of metal loss measurements are desired to be improved.

The method of the invention can be applied to detect both mechanical stress, fatigue, cracks and metal loss, e.g. corrosion in steel. Principally, metal loss and cracks can be monitored in all kinds of electrically conductive materials.

The present invention is based on the idea of deriving information also from the transient curve portion of the voltage or potential drop when monitoring corrosion, erosion and cracks.

During the time when the potential drop over a set of contact points varies after each step of the applied current (excitation current), the potential drop is therefore measured by repeated sampling so that there is obtained a picture of the whole voltage drop curve in the form of a series of number values which can be further processed in a computer. By measuring all the voltage response curves, both the transient part and the stationary part, e.g. for crack monitoring applications, it is possible to detect (follow the development of) deterioration at an early stage and from start of fatigue which is the precursor of cracks. Amongst other things, as such cracks start as micro cracks in the surface and because of the skin effect, the method is most sensitive at the start of the transient voltage response. The method can also be adapted to measure such defects inside the pipe in cases where a measurement unit can be put inside the pipe.

The transient potential drop as a function of time provides information with respect to the electrical and magnetic properties of the steel. When the transient curve after a time interval has completely decayed (the potential drop is then stationary) the level of the potential drop is given by the electric resistance of the steel, which in turn is influenced by cracks and material loss. As already indicated the first portion of the transient curve is mainly related to the magnetic properties of the steel which in turn is influenced by mechanical stresses. In the points listed below it is indicated how magnetic properties of steel are influenced by mechanical stress. The basic physical phenomena and more thorough discussions thereon are available in the literature. (Jiles D. C. and Aderton D. L.: "Theory of the magnetization process in ferromagnets and its application to the magnetomechanical effect", J. Phys. Appl., 17 1984 pp 1265-1281.) The shape or character of both the initial, the anhysteretic and the hysteretic magnetization curve is changed upon the application of mechanical stress.

At a given constant magnetic field strength an applied mechanical stress will make the initial and the anhysteretic magnetization curves approach each other.

The change of magnetization as a consequence of the changed mechanical stress, is not restored when the mechanical stress is reduced to the initial level. Only upon demagnetization by applying a magnetic field with an amplitude gradually diminishing to zero, will the magnetization curves return to their original shape. It has also been shown that the magnetic properties of steel can be influenced during a fatigue process (Bose M. S. C.: "A study of fatigue in ferromagnetic materials using a magnetic hysteresis technique" NOT International Vol. 19 No. 2, April 1986).

The character of the magnetization curves is changed during a fatigue process. These changes cannot be restored by demagnetization.

Measuring relative mechanical stresses in steel can be based on the measurement of the magnetization, (and thus the character of the magnetization curves) under given conditions, for example with reference to the anhysteretic magnetization curve at a given field strength, compared with earlier measurements. The method described in Norwegian patent no. 150136 can then be used. Measurements are then performed also at a location which is not subjected to stress or strain (denoted reference measurement in the above patent). In addition thereto possibilities of demagnetization are incorporated.

A similar method can be employed for measuring the degree of stress to which the steel has been subjected since the last measurement. The property then is utilized that a magnetization change is not restored or reset until demagnetization.

Measurement of absolute mechanical stresses in steel can be based on the fact that the initial magnetization curve and the anhysteretic magnetization curve will be changed upon the application of mechanical stress. The transient voltage drops, which are influenced by the character of the magnetization curves, are measured with reference to both the initial and the anhysteretic magnetization curves, and are compared with each other. In the alternative the two measurements can be made with reference to the hysteretic and the anhysteretic magnetization curves. When there is no mechanical stress in the steel the fatigue condition can be measured in a similar way as absolute mechanical stresses.

To improve accuracy, the response signal can be sampled for several current pulses and by averaging these samples higher accuracy of measurement is achieved. The averaging can be based on applying more or less advanced algorithms. Utilization of the information in the entire response signal, both the transient and stationary part, for all the types of conditions to be monitored, gives improved sensitivity compared to known methods and also in most cases, better accuracy.

Improved crack monitoring is also based on using information in the transient part of the response signal and this achieves improved sensitivity for micro cracks in the surface and furthermore improved accuracy for crack depth determination.

Improved monitoring of metal loss is obtained by observing the entire response signal, both the transient and stationary part, and by this cancel any unwanted effects changing mechanical stress might have on metal loss measurements. Furthermore, using the entire response signal can improve ability of the the method possibility to directly estimate the wall thickness based on the response signal.

Furthermore, significant improvements for detection of micro cracks on the surface of the inner pipe wall are made by connecting one of the excitation current wires and sensing pins on the inner pipe wall.

The method can also be used in sensors. Current feeding and measurements of transient and/or stationary potential drops are then made on e.g. a steel plate attached to the structure or placed in a corrosive environment and thus exposed to relevant stress or corrosion.

A main concept utilized by the present invention as already explained, is the phenomenon that the electrical potential drop curves (both the transient and stationary part) which arise between a pair of contact points as a consequence of applied current pulses, are observed for detection of the structure's condition or change of condition in the steel structure being monitored.

The potential drop for the transient part is related to the skin effect, which in turn is primarily related to the permeability of the steel, and in the stationary part is related to the resistance which in turn is influenced by the object's geometry and also by changes of the structure in the material. (As known, relative permeability is a parameter which indicates the capability of magnetization when a magnetic field is applied).

When applying a current step, for example in a steel plate, the current density at the surface will be high immediately after the current step, and decreases gradually to a stationary value. The potential drop measured between two points will thus reflect the current density at the surface, which is a function of time, having high values initially and decreasing to a stationary value corresponding to the electrical resistance between the measurement points.

Thus, the transient potential drop provides information about both the permeability and the conductivity of the material, which are influenced by mechanical stress and fatigue condition. The electrical resistance is influenced by conductivity and geometry, which again is influenced by metal loss corrosion and erosion and cracks. The different defects have different influences on different parts of the voltage response curve, and by observing the entire response curve, both the transient and the stationary part, sensitivity and accuracy can both be improved compared with the other two mentioned patents.

By observing the entire voltage drop response curve for crack monitoring, significantly improved detection sensitivity for micro cracks on the surface is obtained because of much higher current density at the start of the voltage drop response curve, and later changes in the transient part will give rise to improved estimation of crack position inside the pipe wall and/or crack depth in addition to the information the stationary voltage drop gives about the crack's cross section area. This is in contrast to Norwegian patent no 150136 that mainly only gives information about the cross section area. This is a substantial improvement as crack depth is the most vital information for crack monitoring.

By monitoring the fatigue process the stationary voltage drop gives important supplementary information about changes in the steel structure that causes changes of conductivity. By comparing this with information about deviation of the transient part, a more reliable estimate of the degree of fatigue is achieved.

BRIEF DESCRIPTION OF THE DRAWINGS

The invention is described in more detail below and with reference to drawings where.

DESCRIPTION OF THE PREFERRED EMBODIMENTS

Figure 1:
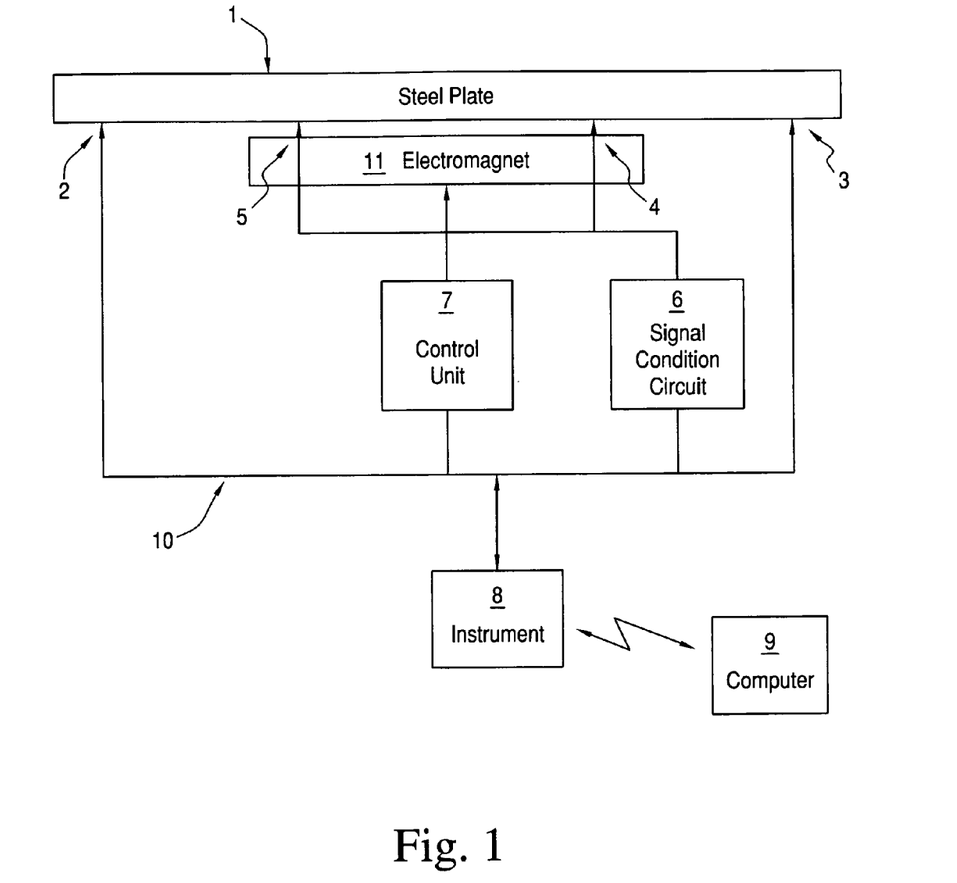
FIG. 1 shows a device for measuring the condition of a steel beam.

To the steel plate 1 in FIG. 1 current pulses (excitation current) is applied by means of the source of current in an instrument 8 through contact points 2,3. When required the source of current in 8 alternatively can be used for demagnetization. Such alternatives can be selected by a menu system in the instrument. By means of this source of current there is applied an alternating current with a amplitude diminishing to zero when used for demagnetization. The potential drop a(t) which is measured between measurement points 4,5 is fed to a signal condition circuit 6 that amplifies and digitises voltages and data is intermediately stored for later transfer to instrument 8 for preliminary processing and for later transfer and further processing in a computer 9. The program in computer 9 has an algorithm for analysing the voltage drop response to calculate mechanical stress and/or fatigue and/or cracks and/or metal loss in the monitored material.

By means of an electromagnet 11 the steel can be magnetized at the location where the potential drop is measured. The strength of the magnetic field applied can be selected as a desired magnitude by means of the software-driven menu system in instrument 8. All direct control of the electromagnet is done by the control unit 7, which again is controlled by the instrument 8. The control function of the menu system of instrument 8, not shown in FIG. 15 may alternatively be a portable PC that is connected to the instrument 8 and is used instead of the instrument 8 for controlling such measurement functions. The connection between the instrument and components connected to the monitored object is a measurement cable 10 that consists of a communication bus and power supply connection. This makes it possible to connect several units to instrument 8 by one connector on one measurement cable 10.

Demagnetization of the steel plate 1 can alternatively be performed by an electromagnet 11 instead of the current source from the instrument 8. As a third alternative the current from the demagnetization source in the instrument 8 can be applied to the steel through contact points which are only employed for this purpose. Current injection points 2, 3, measurement points 4, 5, electromagnet 11 and the circuit modules 6 and 7 can be integrated into one portable unit.

The instrument 8 can be permanently installed for taking measurements at intervals defined in the menu system with intermediate storage of data or transfer of data via an online connection to a user, or via a portable unit to be carried around by the user and by connecting this to fixed mounted equipment taking measurements successively at many such locations. Alternatively all can be portable and the operator will install the unit with current excitation and measurement pins at locations for monitoring, and connect the instrument and measure and finally transfer measurements to a PC for post-processing.

Figure 2:
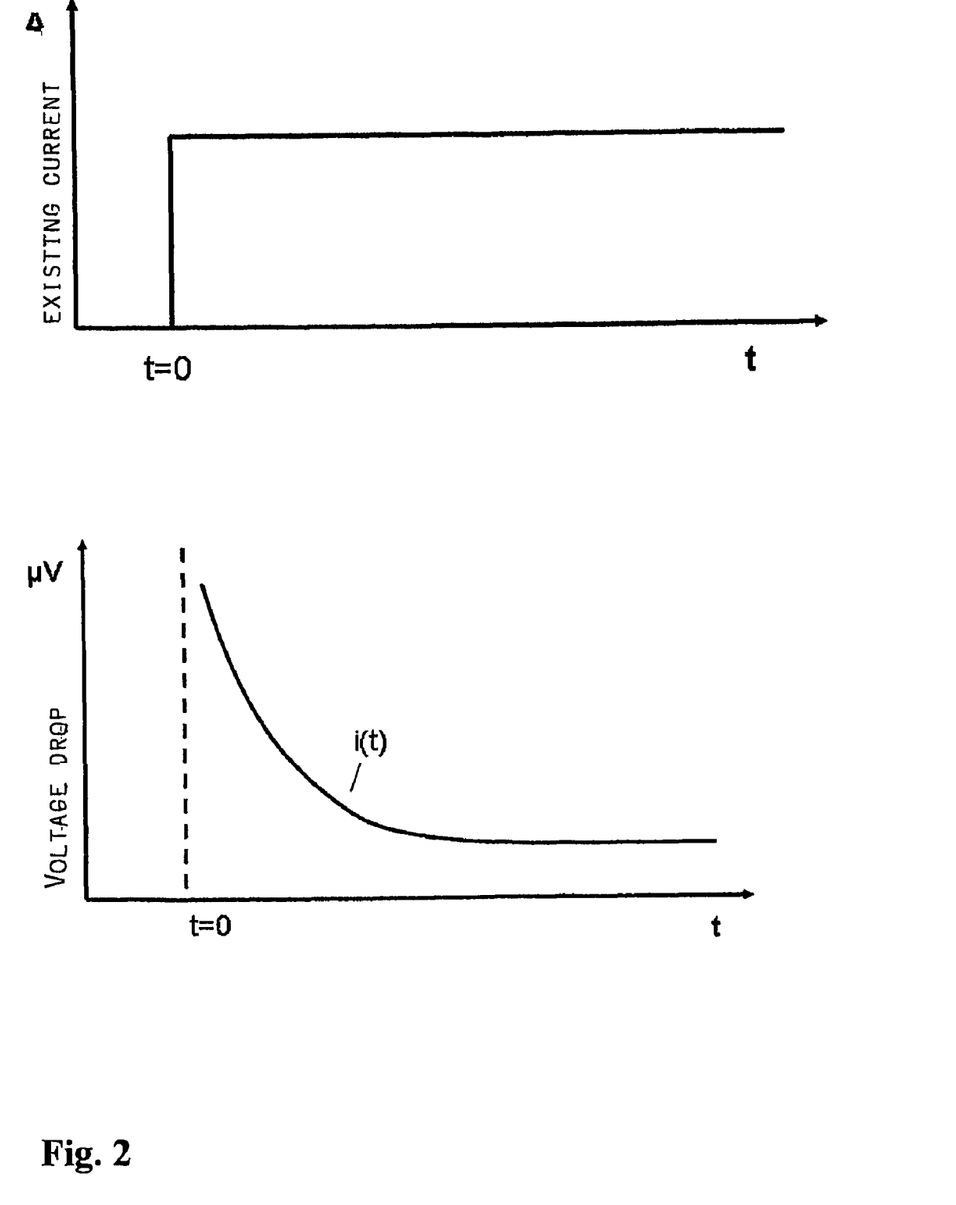
FIG. 2 shows a current step and a voltage drop curve.

In FIG. 2 a typical current step and potential drop are shown with ideal curve shapes. In actual practice the current step will have a certain rise time, and the signal (potential drop) will have an additional component due to electrical induction between measuring leads and the conductor loop which form the application circuit. It is also possible to let the current step start from a negative value.

The potential drop curve according to its nature is a Bessel function. It starts from theoretical infinity, and has a dominating time constant which means that the curve will eventually approach an exponential function. The stationary values which i(t) and a(t) approach, are exclusively determined by the ohmic resistance between the measurement points. The time constant of the exponential function mentioned, is determined by geometrical relationships as well as conductivity and permeability.

If the potential drop is measured at the opposite side of a steel plate in relation to that side where the current step is applied, i(t) will start from zero, and will increase until the stationary value is reached. The analysis of the measurements will always include the comparison of at least two curves as a function of time or frequency.

Figure 3:
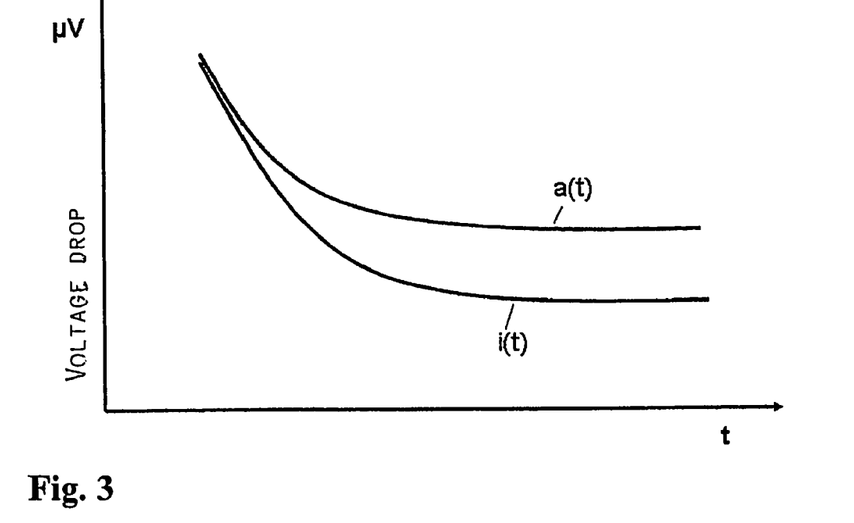
FIG. 3 shows the response voltage for i(t) and a(t) as a function of time. The voltage drops are measured at two different times and where there is wall thickness reduction because of material loss and the same magnetization of the steel.

In FIG. 3 are shown two potential drops i(t) and a(t). Also these are ideal potential drop curves.

Figure 4:
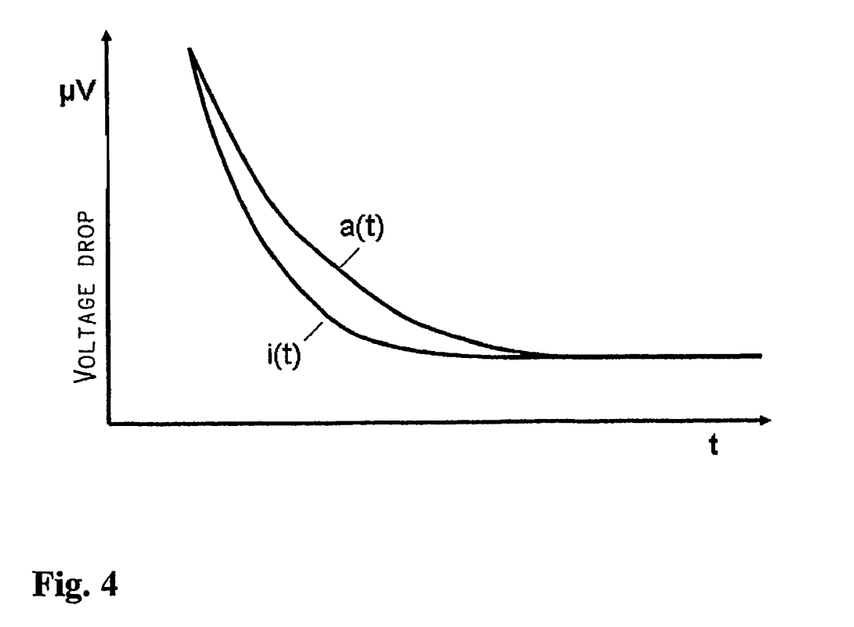
FIG. 4 shows the response voltage for i(t) and a(t) as a function of time for the measurement of absolute mechanical stress, where the voltage responses are measured at two different magnetizations.

FIG. 4 illustrates how, on the basis of two curves i(t) and a(t), a deviation curve d(t), is computed from the difference between the two curves. The deviation curve is computed as $$d(t)=([a(t)/i(t)]-1)1000$$

but other algorithms can also be utilized in order to characterize the deviation between various curves plotted as a function of time.

As an additional explanation referring to FIG. 1 a sequence is described below which explains how the arrangement shown can be employed for measuring such potential drops with reference to the initial and the anhysteretic magnetization curve:

1. The instrument 8 is switched on and initiates the setting of all output signals to zero.
2. The current source in the instrument 8 is activated for demagnetization.
3. The excitation current source in the instrument 8 injects the pulse shaped current to the steel 1 at current applications points 2, 3.
4. The transient and stationary potential drop between measurement points 4, 5, a(t), is measured and stored in the instrument 8.

5. The current from the current source in the instrument 8 to current control unit 7 for the magnetization current to the electromagnet 11 is continually increased to the desired magnitude. The steel is now magnetized with reference to the initial magnetization curve.

6. The above step 3 is repeated.

7. The transient potential drop between measurement points 4, 5, i(t), is measured and stored in the instrument 8.

8. FIG. 4 shows typical voltage drop curves for i(t) and a(t).

9. Preliminary computation of d(t) can be done in the instrument 8.

10. All measurements are transferred to computer 9 for computation of d(t) and other postprocessing.

Figure 5:
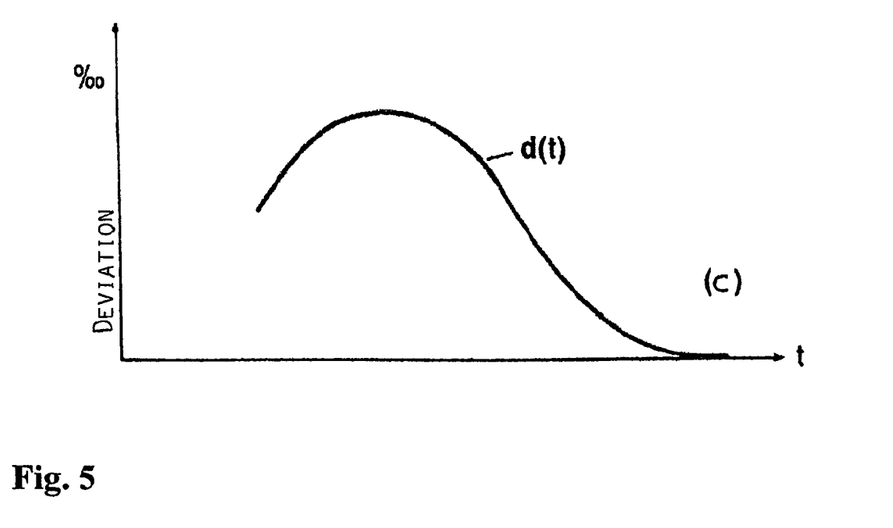
FIG. 5 shows the calculated deviation curves for the voltage response curves in FIG. 4.

11. In FIG. 5 is shown a typical deviation curve d(t) for measurement of stress in steel.

12. From the deviation curve d(t) the maximal value is found and this represents the stress in the steel.

The deviation curve where only mechanical stress is present is characterized by the deviation after a time period to reach a maximum value and thereafter decays to d(t)=O where the voltage drop is stationary. If desired it is also possible to compute deviation curves with reference to the initial and the hysteretic magnetization curves. From experience the characteristics of the deviation curves at different mechanical stresses is known and make it possible to determine the unknown stress condition.

Measurement of relative mechanical stress in steel, can be based on magnetization, and thus the magnetization curve for known conditions, e.g. with reference to the anhysteretic magnetization curve for a given magnetic field strength, is measured and compared with previous measurements. Usually such measurements are done by also taking measurements at a point not exposed to loads and which is described as reference readings in the mentioned patent. In addition possibilities for demagnetization are included.

A similar method can be used for measurement of the maximal stress the steel has been exposed to since the last measurement. The change of magnetization as a consequence of the changed mechanical stress, is not restored when the mechanical stress is reduced to the initial level. Only upon demagnetization will the magnetization curves return to their original shape.

Measurement of absolute mechanical stresses in steel can be based on the fact that the initial magnetization curve and the anhysteretic magnetization curve will be changed upon the application of mechanical stress. The transient voltage drops, which are influenced by the character of the magnetization curves, are measured with reference to both the initial and the anhysteretic magnetization curves, and are compared with each other. Alternatively two measurements can be made with reference to the initial and the hysteretic magnetization curves.

Figure 7:
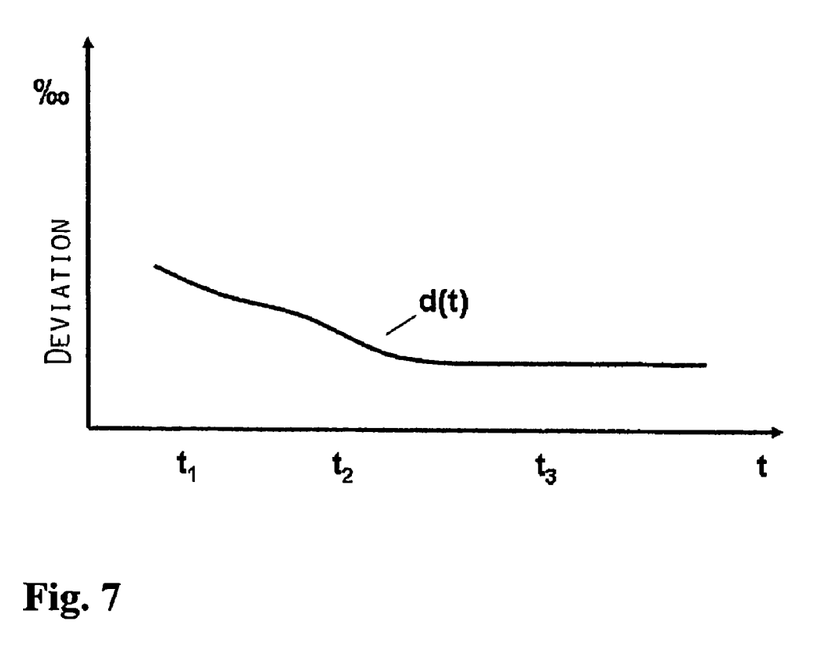
FIG. 7 shows a calculated deviation curve that is typical for fatigue.

The deviation curves can in similar ways be used to estimate the steel's fatigue condition and thus on this basis compute remaining lifetime before fracture in a fatigue process. When there is no mechanical stress in the steel e.g. the fatigue condition can be measured in a way similar to absolute mechanical stresses. It can also be measured with the same method as applied when measuring relative mechanical stress. By observing the deviation curves in FIG. 7 for the entire potential drop duration, additional information about the degree of fatigue is obtained. One example of deviation curves for relative measurement of fatigue is shown in FIG. 7. The level at ti represents the degree of micro cracks in the surface, the level at t2 represents the degree of change of the ferromagnetic properties first of all the permeability, while t3 shows the relative change of resistance, which for fatigue is caused by structural changes in the steel. Another characteristic symptom of fatigue is the relative levels of deviations at t2 related to deviation at t3 when deviations are calculated for measurements taken before and after demagnetization. The less relative deviation, the more fatigue has developed.

Measurement of metal loss, corrosion or erosion, can be done without magnetization and can also be done without demagnetization if the measurement can be done in the stationary part of the potential drop or if there have been no changes in mechanical stress of the monitored object since the last measurement.

Figure 6:
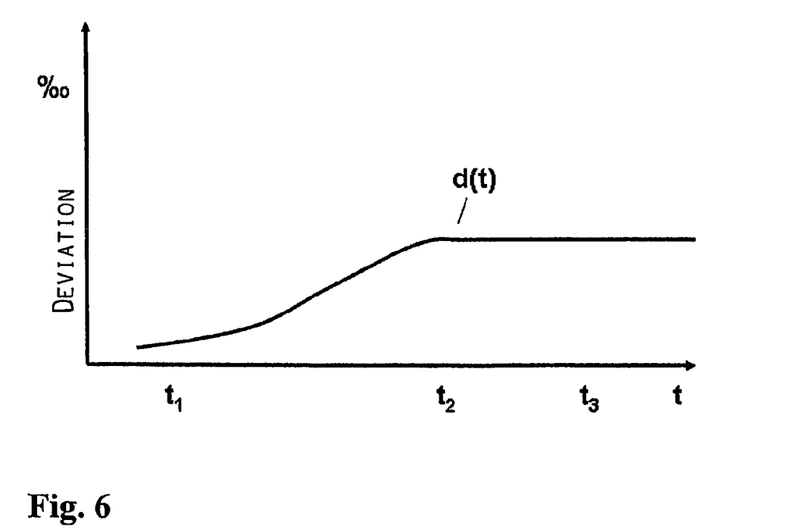
FIG. 6 shows the calculated deviation curves for the voltage response curves in FIG. 3 and is typical for corrosion or erosion.

In FIG. 6 is shown a characteristic potential drop deviation curve for relative measurement of metal loss. The deviation value at ti represents any changes of mechanical stress. The time for t2 where there is a significant break in the deviation curve can be used for estimation of the wall thickness. The deviation's stationary level at t3 represents metal loss related to the measurement used as reference data for the deviation calculation.

The invention claimed is:

1. A method for measuring different condition parameters in an electrically conductive material over an extended period of time or absolute momentary measurements for detection of mechanical stress and defects and deterioration, comprising the steps of:
    impressing a pulse shaped electrical current between at least two first contact points, and measuring a transient part and a stationary part of a drop in electrical voltage between other pairs of installed contact points; and
    comparing the measured voltage drop with another voltage drop measured under known measurement conditions, or comparing the measured voltage drop with calibration data for the material, and analyzing deviations therebetween to determine the condition of the material.

2. A method as claimed in claim 1, additionally comprising providing means for magnetizing the material, and means for demagnetizing the material.

3. A method as claimed in claim 2, comprising demagnetizing the material with alternating current before determining the condition of the material.

4. Method as claimed in claim 2, wherein the means for magnetization or means for demagnetization is an electromagnet.

5. A method as claimed in claim 1, wherein both initial and later measurements are carried out at a location which is subjected to mechanical load or deterioration and at a location which is not loaded or deteriorated, and the results of these measurements are utilized to determine the change in the mechanical stress and/or the fatigue condition and/or cracks and/or material loss in the material in relation to that at the time of the initial measurement.

6. A method as claimed in claim 1, wherein initial and later measurements are carried out both at a location which is subjected to mechanical load or deterioration, and a piece of reference material that is not loaded or deteriorated, and the results of these measurements are utilized to determine the change in the mechanical stress and/or the fatigue condition and/or cracks and/or material loss in the material in relation to that at the time of the initial measurement.

7. A method as claimed in claim 1, comprising performing a measurement on a location on an object that has been exposed to mechanical stress, comparing the measurement with a previous measurement taken at the location, a measurement taken after demagnetization of the location, or after at least one voltage pulse has been impressed on the location, and analyzing the difference between these measurements to determine the maximum mechanical load the material has been subjected to since last such measurement.

8. A method as claimed in claim 1, comprising installing units at certain distances along a structure to monitor changes of structure condition both along the structure and during a time period.

9. A device for the implementation of the method as claimed in claim 1, comprising means for feeding an electrical current to the material through the first contact points, a set of measurement electrodes constructed and arranged for connection for measuring the voltage drops, and means for recording and analyzing measurement results, wherein the means for recording and analyzing are constructed and arranged to measure transient and stationary voltage drops and includes algorithms for analyzing the voltage drops to determine mechanical stress and/or fatigue condition, and/or cracks and/or material loss in the material.

10. A device as claimed in claim 9, additionally comprising means for magnetizing and means for demagnetizing the material.

11. A device as claimed in claim 10, additionally comprising means to apply voltage pulses, constructed and arranged to impress a pulse-shaped voltage between the pair of contact points and alternatively impress alternating voltage at the pair of contact points, with amplitude gradually diminishing to zero, to demagnetize the materials.

12. A device as claimed in claim 10, constructed and arranged to magnetize the materials at selected points of an initial, anhysteric or hysteric magnetization curve at a selected location, including means for measuring the voltage drop caused by impressed pulses with reference to at least one magnetization curve, the measurement being applied to determine the condition of the materials.

13. A device as claimed in claim 9, constructed and arranged to be inserted in a pipe from an end thereof for connection of a current feeding connection inside the pipe, comprising an array of measurement electrodes which is connected inside the pipe to measure the voltage drop on the inside giving better sensitivity for micro cracks on the inside surface.

\* \* \* \* \*